United States Patent [19]

Meijer

[11] Patent Number: 4,658,244
[45] Date of Patent: Apr. 14, 1987

[54] AIR-IN-LINE DETECTOR

[75] Inventor: Robert Meijer, San Diego, Calif.

[73] Assignee: IMED Corporation, San Diego, Calif.

[21] Appl. No.: 716,862

[22] Filed: Mar. 28, 1985

[51] Int. Cl.⁴ .............................................. G08B 17/10
[52] U.S. Cl. .................... 340/632; 73/861.04; 128/DIG. 13; 356/39
[58] Field of Search ................ 340/603, 632; 250/575, 250/573; 128/DIG. 13; 356/39; 73/861.04

[56] References Cited

U.S. PATENT DOCUMENTS

| | | | |
|---|---|---|---|
| 2,835,252 | 5/1958 | Mauchel | 128/214 |
| 3,480,784 | 11/1969 | Pierce | 250/218 |
| 3,812,482 | 5/1974 | Clark | 340/237 R |
| 3,898,637 | 8/1975 | Wolstenholme | 340/239 R |
| 3,935,876 | 2/1976 | Massie et al. | 137/177 |
| 3,974,683 | 8/1976 | Martin | 73/432 PS |
| 4,080,967 | 3/1978 | O'Leary | 128/214 F |
| 4,112,735 | 9/1978 | McKnight | 73/19 |
| 4,114,144 | 9/1978 | Hyman | 340/632 |
| 4,126,132 | 11/1978 | Portner et al. | 128/214 F |
| 4,138,879 | 2/1979 | Liehermann | 73/19 |
| 4,210,138 | 7/1980 | Jess et al. | 128/214 E |
| 4,256,437 | 3/1981 | Brown | 417/45 |
| 4,265,240 | 5/1981 | Jenkins | 128/214 E |
| 4,280,495 | 7/1981 | Lampert | 128/214 E |
| 4,312,341 | 1/1982 | Zissimopoulos et al. | 128/214 E |
| 4,344,429 | 8/1982 | Gupton et al. | 128/214 R |
| 4,366,384 | 12/1982 | Jensen | 250/575 |
| 4,367,736 | 1/1983 | Gupton | 128/214 E |
| 4,384,578 | 5/1983 | Winkler | 604/114 |

Primary Examiner—Glen R. Swann, III
Assistant Examiner—Jeffery A. Hofsass
Attorney, Agent, or Firm—Workman, Nydegger & Jensen

[57] ABSTRACT

A detector for automatically determining the presence of air in a fluid line comprises a plurality of ON-OFF optical sensors selectively disposed in series along the axis of a portion of an I.V. tube according to their relative light sensitivity and according to their dependence upon direct or refracted light for activation. An alarm condition indicates air-in-line when predetermined individual sensors change their ON or OFF condition in accordance with a microprocessor programmed logic sequence.

10 Claims, 11 Drawing Figures

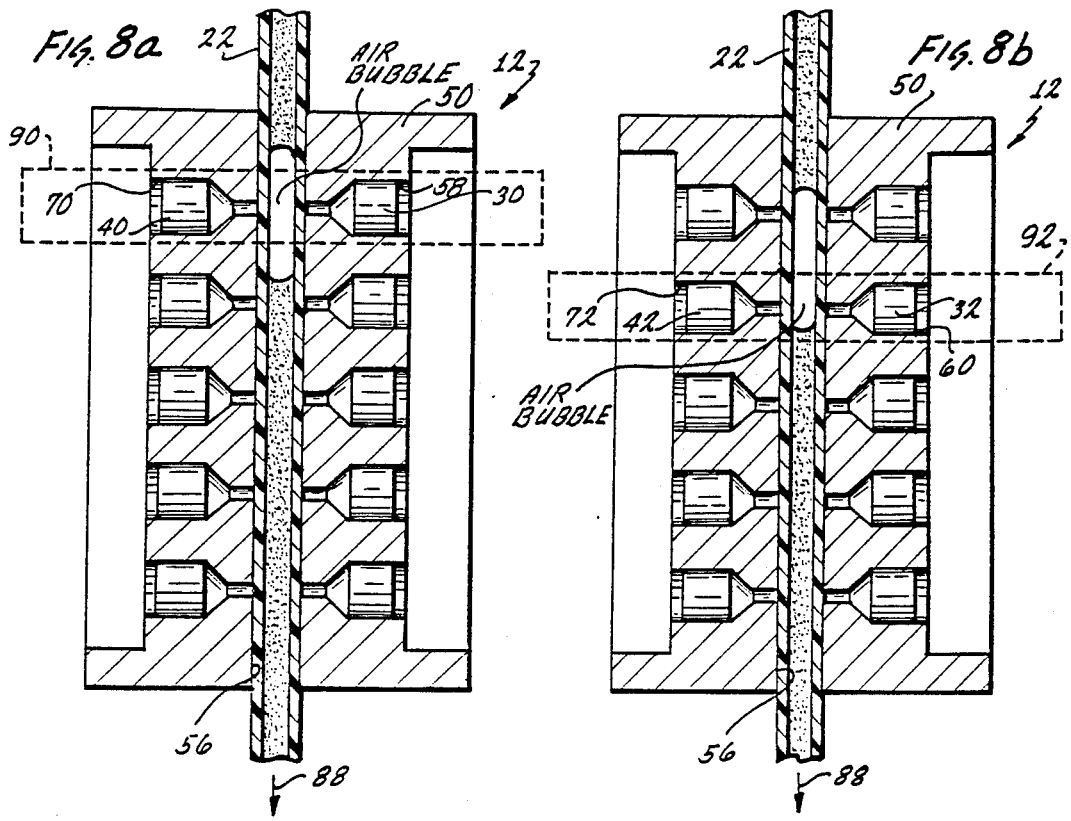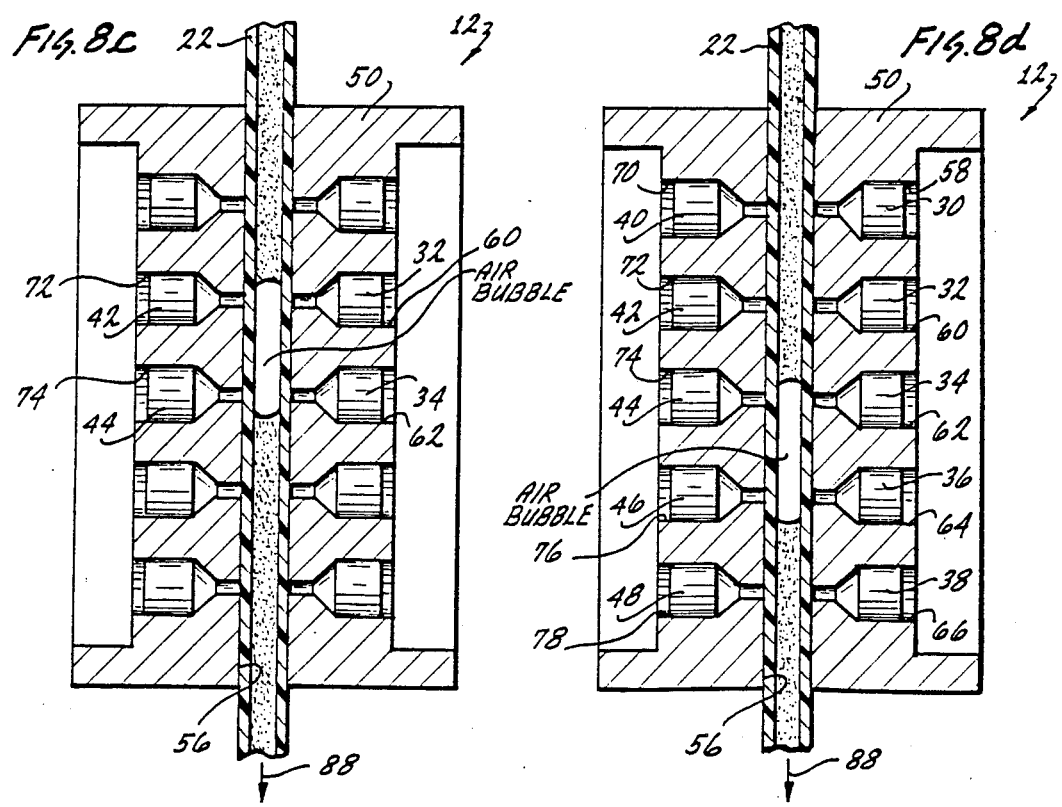

AIR-IN-LINE DETECTOR

BACKGROUND OF THE INVENTION

This invention relates generally to air-in-line detectors. Specifically, the present invention relates to an air-in-line detector which uses a series of optical sensors spaced axially along a fluid flow line and having selectively different light sensitivities and selectively different optical path arrangements to provide a sequence of signals for determining whether an air bubble is present in the fluid flow line. More specifically, the present invention relates to an air-in-line detector which is insensitive to changes in the level of ambient light and which can determine the presence of air bubbles in a fluid line regardless of the opacity or opalescence of the fluid. This invention is particularly, but not exclusively, suited for use with an I.V. infusion pump or controller to determine the presence of air bubbles in the I.V. administration fluid flow line.

DESCRIPTION OF THE PRIOR ART

During the infusion of I.V. fluids to a patient, it is important that the fluid flow line be monitored to insure that a minimum amount of air is infused with the fluid. Although a small amount of air may inadvertently be infused to the patient without adverse effects, the infusion of relatively larger amounts of air can be extremely dangerous. Thus, as has been previously recognized, it is important to provide a means to determine whether air is present in the I.V. fluid flow line.

Various apparatus and methods have been suggested to solve the air-in-line problem. For example, U.S. Pat. No. 3,898,637 to Wolstenholme suggests using an electrical conductivity indicator to determine whether there is an air-in-line condition. U.S. Pat. No. 2,573,390 to Blanchard suggests using a detector for compression wave propogation for this purpose. Further, U.S. Pat. No. 3,974,683 to Martin discloses use of an ultrasonic detector, and U.S. Pat. No. 4,384,578 to Winkler suggests the use of a temperature differential indicator to determine the presence of air in a fluid line. Additionally, like the present invention, various arrangements have been proposed which use optical sensors to detect the presence of air in a fluid line.

Four separate states or conditions of flow through the I.V. tubing can be identified during the administration of I.V. fluid to a patient. Briefly, these conditions are: (a) clear fluid in line, (b) opaque fluid in line, (c) fluid in line which is somewhere between being clear or opaque such as an opalescent or translucent fluid, and (d) air in line. Of course, the object of an accurate and reliable air-in-line detector is to distinguish any of the first three conditions from the air-in-line condition.

If a clear plastic I.V. administration tubing set is used, optical sensors will provide signals which can be interpreted by logic circuitry to indicate certain flow conditions. An example of such an arrangement is disclosed in U.S. Pat. No. 4,366,384 to Jensen. Also, U.S. Pat. No. 4,114,144 to Hyman which is assigned to the assignee of the present application discloses a device for detecting air-in-line conditions using optical sensors. These references both rely on the refractive properties of fluids and the ability of an opaque fluid to occlude a light path. For instance, it is well known that an optical sensor which comprises a light emitter that directs light diametrically through clear tubing to a light detector will discriminate between conditions which block the path of light and those that do not. Thus, such a sensor can distinguish between an opaque fluid in the line which blocks the light beam and air in the line which allows light from the emitter to pass to the detector. This direct path arrangement, however, would not differentiate between a clear fluid and air unless the detector is somehow sensitized to detect increased light intensity caused by the focus effect of clear fluid in the line. The focus effect, however, becomes increasingly negligible with an increase in opalescence or opacity of the fluid. In fact, increased fluid opacity will eventually make the sensor ineffectual to distinguish between air and fluid in the tubing.

The earlier references have also found that an optical sensor can be structured to work with a refracted or indirect light path. In such a sensor the light from a light emitter is directed substantially tangential to the fluid column and a light detector, located diametrically opposite the emitter on the other side of the tube, will complete the optical path between emitter and detector only when a clear fluid is in the tube to refract the light beam. This refracted path arrangement, unlike the direct path arrangement discussed previously, is capable of differentiating between clear fluid and air in the tubing. The refracted path arrangement, however, does not differentiate between air and an opaque fluid since in either case light does not reach the detector. Further, like the direct path arrangement, the refracted path arrangement becomes unreliable at the point where a translucent or opalescent material is in the line and light is blocked rather than refracted.

The present invention recognizes that there is a need for an air-in-line detector which can make the general distinction between air and fluid regardless of the opacity of the fluid. Additionally, the present invention recognizes that where optical sensors are used in an air-in-line detector, changes in the level of ambient light may activate or deactivate a light detector to give a false indication of the actual condition.

Accordingly, the present invention has addressed the problems of changing ambient light levels and opalescent fluid in line and has determined that the broad distinction between fluid and air in an I.V. line can be made, under any light condition and regardless of the opacity of the fluid, by selectively arranging optical sensors in series according to their sensitivity to light and according to their dependence on direct or refracted light for activation. Further, the present invention contemplates that a microprocessor logic program will provide information for an accurate indication of air-in-line in accordance with the sequencing of changes in the ON-OFF state of various individual sensors.

SUMMARY OF THE INVENTION

An object of the present invention is to provide a reliable air-in-line detector for an I.V. fluid line which provides an accurate indication of air-in-line regardless of the opacity or opalescence of the fluid being administered through the fluid line. Another object of the present invention is to provide an air-in-line detector which is insensitive to ambient light levels and will therefore continue to provide accurate indications of the absence or presence of air in the fluid line despite changes in the ambient light level. It is yet another object of the present invention to provide an air-in-line detector that is relatively inexpensive and easy to manufacture and which is simple to operate.

According to the present invention, a detector for automatically determining the presence of air in a fluid line is provided which comprises a first ON-OFF optical sensor having a light emitter and a light detector which are operatively associated with an I.V. fluid line to produce ON-OFF signals according to whether light can travel a direct line optical path between the director and the sensor. An ON signal is indicated when either air or a clear fluid is present in the fluid line. The detector of the present invention also includes a second ON-OFF optical sensor having a light emitter and a light detector which are operatively associated with the I.V. tube downstream from the first optical sensor. The second optical sensor has a relatively lower light threshold than the first optical sensor, and it produces ON-OFF signals according to whether light can travel a refracted optical path from its emitter to its detector. An ON signal is indicated for the second sensor when a relatively clear fluid is in the line which will refract light from the emitter and direct it to the detector. Accordingly, an OFF signal is indicated when light from the emitter is not refracted toward the detector, as when air is in the line, or a relatively opaque fluid is in the fluid line to block the light from reaching the detector. The automatic air-in-line detector of the present invention also includes a microprocessed logic circuitry which is operatively connected with the first and second optical sensors to alarm and stop operation of the fluid infusion apparatus in accordance with pre-programmed sequencing of ON-OFF signals from the first and second optical sensors. As will be appreciated by the skilled artisan, a plurality of optial sensors can be arranged axially along the fluid path in accordance with the present invention to provide for redundancy in the system.

The novel features of this invention, as well as the invention itself, both as to its organization and operation will be best understood from the accompanying drawings taken in conjunction with the accompanying description in which similar reference characters refer to similar parts and in which:

BRIEF DESCRIPTION OF THE DRAWINGS

FIGS. 8a, b, c and d successively illustrate a cross-sectional view of the portion of the automatic detector taken along lines 8—8 of FIG. 3 or FIG. 4 as an air bubble progresses through an associated fluid line.

DESCRIPTION OF THE PREFERRED EMBODIMENT

Figure 1:
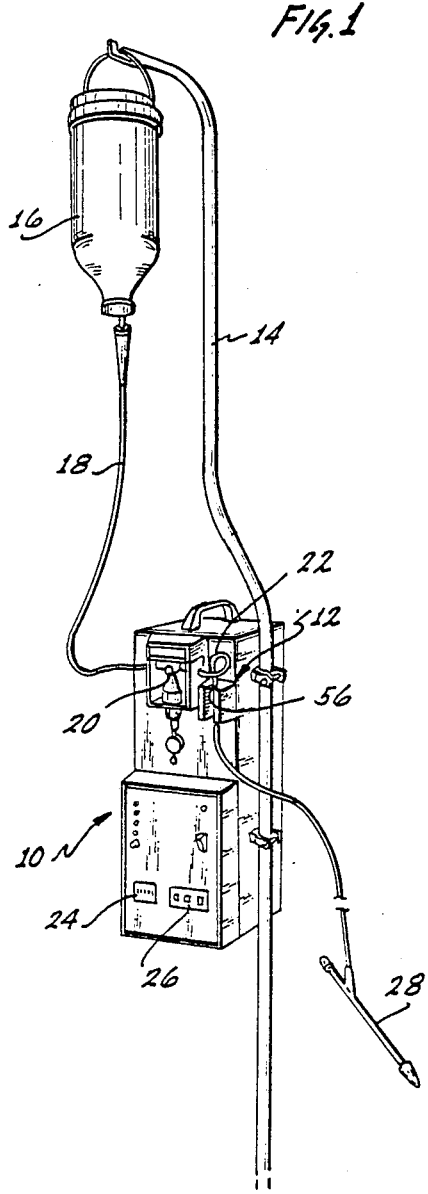
FIG. 1 illustrates an I.V. administration system including a volumetric infusion pump with an automatic air-in-line fluid detector of the present invention.
Figure 2:
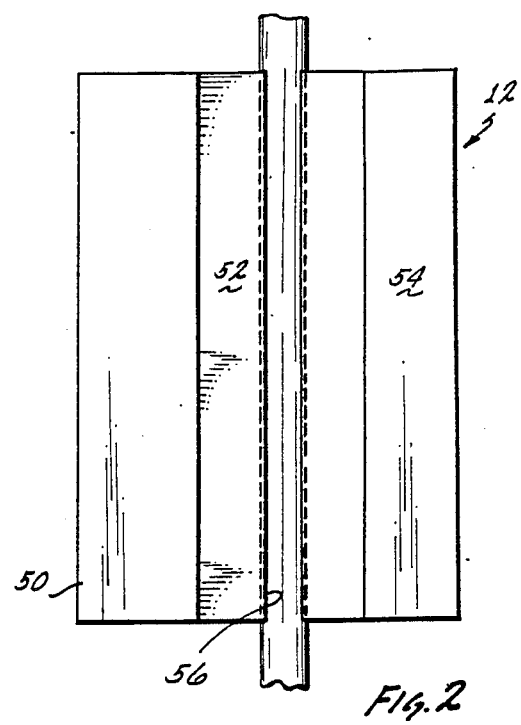
FIG. 2 illustrates a front view of an external portion of the automatic detector of the present invention which portion receives the fluid line.
Figure 3:
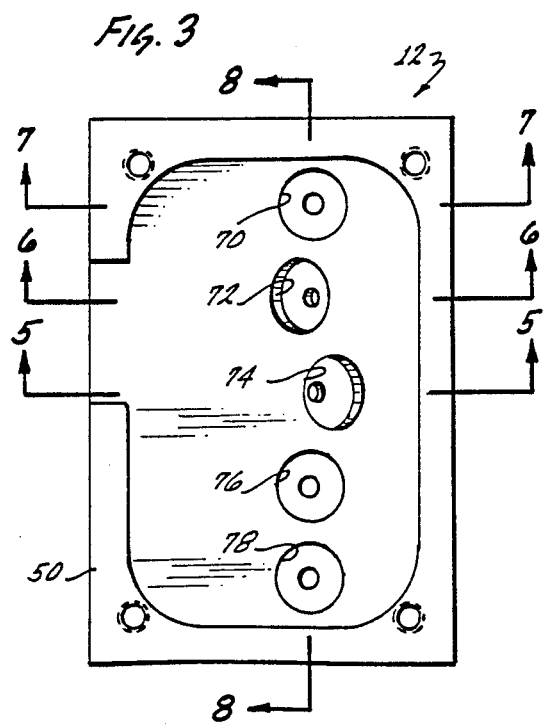
FIG. 3 illustrates a left side view of the portion of the automatic detector of FIG. 2.

In FIG. 1 a volumetric pump 10 is shown. Pump 10 may include an automatic air-in-line fluid detector having a support portion 12 for receiving a fluid line 22. As seen in FIG. 1, pump 10 is mounted on a pole 14 and a bottle of fluid 16 to be infused is supported above the pump 10. Fluid from the bottle 16 is allowed to flow downward through a fluid line 18 and enter a disposable cassette 20. During normal operation pump 10 provides for an accurate pumping of the fluid from the cassette 20 to an outside fluid line 22.

The pump 10 may include a pair of dials, such as dials 24 and 26, which control the rate of fluid flow to the fluid line 22 and the volume of fluid which is to flow through the line 22 to the patient. At the end of the line 22 is provided means 28 for allowing infusion of the fluid to the patient. For example, means 28 may include a hypodermic needle which is used to infuse fluid into the vein of the patient. The pump 10 may be of the type disclosed in U.S. Pat. No. 3,985,133, which is assigned to the same assignee as the instant application. It is to be appreciated, however, that the automatic air-in-line fluid detector of the present invention may be used with other types of fluid pumps. Further, the automatic air-in-line detector of the present invention may be used with any type of gravity feed means for infusing fluid to a patient, such as a controller.

The fluid line 22 passing from the cassette 20 is positioned within a channel 56 in the support portion 12. The support 12 includes a plurality of detector elements which in combination with appropriate electronic circuitry provide for an automatic detection of air-in-line.

FIGS. 2 through 7 show the details of the construction of the support 12. As illustrated, support 12 includes a base 50 having an open front with a pair of tapered sides 52 and 54 leading to circular channel 56 which channel receives the fluid line 22 in a position for detection of the contents passing through line 22. A plurality of light emitters and light detectors are disposed along the channel 56 on opposite sides of the channel to provide for the detection of air-in-line regardless of the opacity of the fluid normally in the line 22.

Figure 4:
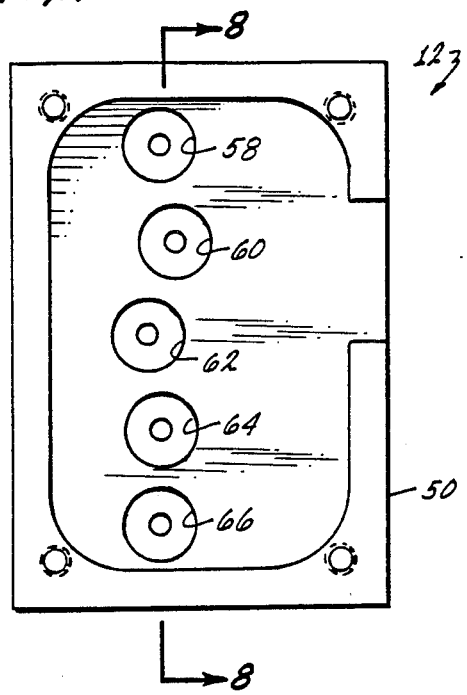
FIG. 4 illustrates a right side view of the portion of the automatic detector of FIG. 2.

As best seen in FIG. 4 and FIGS. 8a, b, c and d, a plurality of light emitters 30, 32, 34, 36 and 38 (not shown in FIG. 4) are respectively positioned in a plurality of emitter openings 58, 60, 62, 64 and 66 in base 50 which optically communicate with one side of the channel 56. Base 50 is also provided with a recess portion 68 to provide access to the openings 58, 60, 62, 64 and 66 to properly position the light emitters 30, 32, 34, 36 and 38 and to provide for the necessary electrical wiring (not shown) to the light emitters. Light emitters of a type well known in the art, such as Model No. SE-5455-3 manufactured by Spectronics, can be used for the present invention. Also, it will be appreciated that these light emitters may be light emitting diodes which provide for a light output spectrum in the infrared range. Although either visible or invisible light can be used, since certain drugs are light sensitive, the infrared light spectrum may be preferred in order to provide for a proper detection without damaging the drug solutions.

On the opposite side of the channel 56, as seen in FIG. 4 and FIGS. 8a, b, c and d, a plurality of light detectors 40, 42, 44, 46 and 48 (not shown in FIG. 4) such as phototransistors having a light detection spectrum complementary to the light emitters are respectively positioned in a plurality of detector openings 70, 72, 74, 76 and 78 which optically communicate between a recessed area 80 in base 50 and the channel 56. Light detectors or photo transistors of a type well known in the art, such as Model No. SPX-2532 manufactured by Spectronics, will serve the purposes of the present invention.

Important to the present invention is that the detectors 42 and 44, positioned respectively in openings 72 and 74, are more sensitive to light than are the detectors 40, 46 and 48. In other words, detectors 42 and 44 will change from an OFF condition (absence of light) to an ON condition (detection of light), and vice versa, at a lower threshold of light intensity, or higher degree of fluid opacity, than required to change the ON-OFF condition of detectors 40, 46 and 48. It will be appreciated by the skilled artisan that the same result can be accomplished by effectively increasing the intensity of emitters 32 and 34 relative to emitters 30, 36 and 38. If this is done, the sensitivity of detectors 40, 42, 44, 46 and 48 may all be the same or varied as discussed above. There are several ways, all well known in the pertinent art, by which detector sensitivity and emitter intensity can be varied to accomplish the purposes of the present invention.

Figure 7:
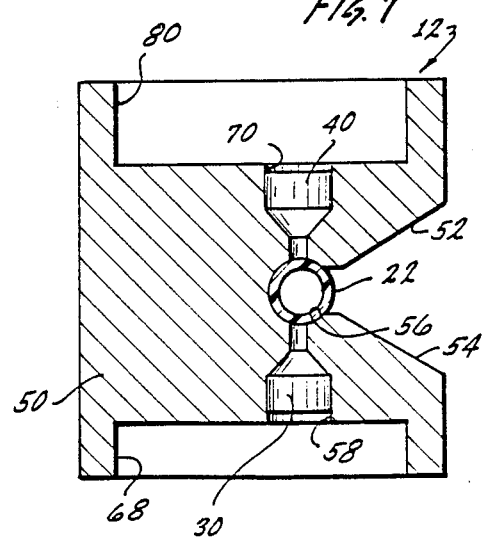
FIG. 7 illustrates a cross-sectional view of the portion of the automatic detector taken along lines 7—7 of FIG. 3.

It should also be noted that the emitters 30, 36 and 38 and respective detectors 40, 46 and 48 are aligned along the same axis for providing a direct optical path substantially along the diameter of a cross-sectional area of the fluid line 22, such as shown for emitter 30 and detector 40 in FIG. 7. Thus, as previously discussed, if an opaque fluid is present in the portion of fluid line 22 positioned in the channel 56, little or no light energy passes from one of the emitters to one of the detectors. If, on the other hand, a transparent fluid or air is present in the portion of fluid line 22 positioned in the channel 56, light energy freely passes from an emitter to its complementary detector arranged as shown in FIG. 7. The emitters and detectors positioned in openings 64, 66, 76 and 78 are arranged along the same axis in the same way as that shown in FIG. 7.

Figure 5:
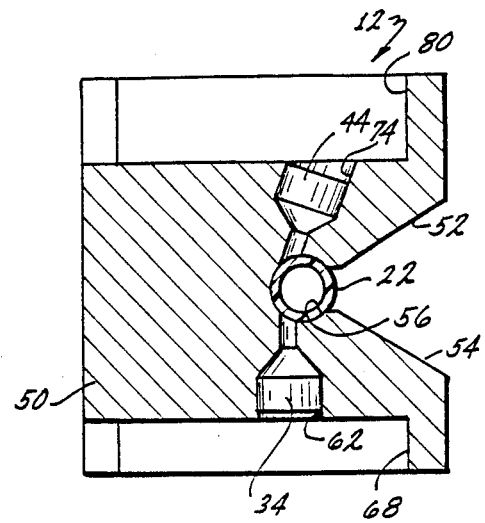
FIG. 5 illustrates a cross-sectional view of the portion of the automatic detector taken along lines 5—5 of FIG. 3.
Figure 6:
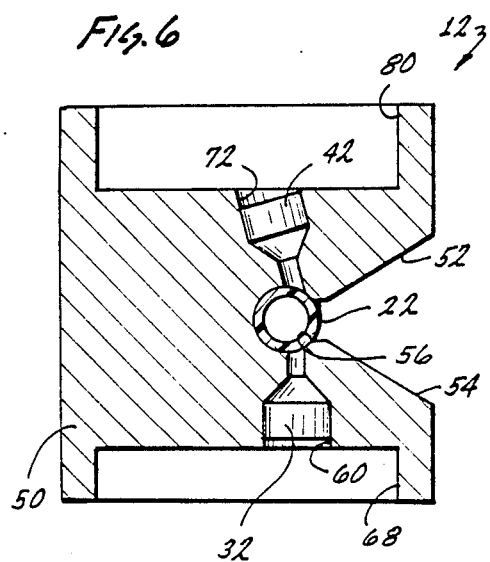
FIG. 6 illustrates a cross-sectional view of the portion of the automatic detector taken along lines 6—6 of FIG. 3.

For purposes discussed previously, emitters 32 and 34 and detectors 42 and 44 are offset from each other. Specifically, with reference to FIG. 5, emitter 34 in opening 62 is arranged to direct light energy through the channel 56 but at a rearward position of the channel 56. In addition, the detector 44 is set at an angle. When there is a transparent fluid in the line 22, the light from emitter 34 is refracted by the fluid to pass to detector 44. However, if air is in tube 22, the light from emitter 34 is not refracted and it does not pass to the detector 44. The operation of the emitter 32 and detector 42 in the openings 60 and 72 shown in FIG. 6 are essentially similar to that shown in FIG. 5 and described above except they are located to the front of the channel 56. The positioning of these emitters and detectors ensures detection on both sides of the fluid line 22 and enables the detector to detect larger air bubbles but allow small air bubbles which are not harmful to pass.

OPERATION

The operation of the present invention is best understood by initially considering the operation of only two optical ON-OFF sensors included in the preferred embodiment of the present invention. For this purpose, the light emitters 30 and 32 and their respectively associated detectors 40 and 42 will be discussed. As seen in FIG. 8a, light emitter 30 and light detector 40 together comprise a first optical sensor 90. Also, as seen in FIG. 8b, light emitter 32 and light detector 42 together comprise a second optical sensor 92. As shown in FIGS. 8a, b, c and d, first optical sensor 90 is positioned upstream from second optical sensor 92. Accordingly, the leading edge of an air bolus in the fluid line 22 will pass first optical sensor 90 before passing second optical sensor 92.

As previously stated, detector 40 of first optical sensor 90 is adjusted to a higher light intensity than is detector 42 of second optical sensor 92. In other words, as light intensity dims, optical sensor 90 will change to an OFF condition (no detection of light) before optical sensor 92. Also, as previously disclosed, it is necessary that first optical sensor 90 be arranged in a manner as shown in FIG. 7 for a direct light path diametrically through the lumen of the I.V. tube 22. This direct path arrangement minimizes or eliminates any refraction of the light path by fluid in the line. Additionally, it is important that second optical sensor 92 be arranged as shown in FIG. 5 or FIG. 6 so that the passage of light from emitter 32 to detector 42 is dependent upon a refracted light beam. As can be appreciated by the skilled artisan, second optical sensor 92 will not pass light when there is either air in fluid line 22, since air does not effectively refract light, or when there is a sufficiently opaque fluid in the line 22 which will not effectively pass the light ray.

The logic circuitry required in a microprocessor (not shown) to accomplish the purposes of the present invention can be best understood by reference to Logic tables. It is understood that various microprocessor programs can be generated by the skilled artisan to accomplish the purposes of the present invention in accordance with the disclosed logic. Although several microprocessors are available, for the purposes of the preferred embodiment, microprocessors of the type 8051 manufactured by Intel Corporation and identified by MCS Series are preferred.

TABLE I

| Sensor Condition: Initially Clear Fluid | | | |
|---|---|---|---|
| | Clear Fluid in Line | Increased Opacity or Decrease in Ambient Light | Air-in-Line |
| First Sensor (direct) | ON | OFF | ON |
| Second Sensor (refracted) | ON | ON | OFF |
| | | NO ALARM | ALARM |

Table I assumes an initial condition wherein a clear fluid is passing through the fluid line 22 in a direction indicated by the arrow 88 in FIGS. 8a, b, c and d. Under this condition, both first sensor 90 and second sensor 92 are in the ON condition indicating that light from the emitter of each optical sensor is being sensed by the detector of each sensor. Also shown in Table I is the effect of an increase in the opalescence or opacity of the fluid passing through the I.V. line 22. Under this situation, sensor 90 will change to the OFF condition before sensor 92 because sensor 92 requires less light intensity for the ON condition than does sensor 90. In this situation there should be no alarm. Another situation which can affect sensors 90 and 92 when a clear fluid passes through the fluid line 22 is, a change in the ambient light. An increase in ambient light will have no effect upon either sensor 90 or sensor 92 since both detectors 40 and 42 have already exceeded their threshold for sensing light. However, in situations where there is a decrease in the ambient light, if a sensor is affected, sensor 90 will be the first to change to the OFF position. It should be appreciated that this may happen although there is still fluid within the fluid line. Again, there should be no alarm. In the situation where there is an air bubble in the clear fluid in the line 22, sensor 90 will remain ON as the bubble passes because the presence of air in the line 22 does not disrupt its light path. On the other hand, as the bubble passes sensor 92, light from its emitter 32 is no longer refracted due to the absence of fluid in the line. Since detector 42 no longer senses light from the emitter 32, sensor 92 turns OFF. In this situation, i.e., sensor 90 ON and sensor 92 OFF, there is air in the line and an alarm should be indicated.

Using this information, a logic program could be established in a microprocessor by a skilled artisan whereby an alarm is activated whenever sensors 90 and 92 are initially in an ON condition and then sensor 92 turns to an OFF condition. Logic circuitry can be established to ignore changes in sensor 90 from ON to OFF which would only indicate either increased opacity in fluid line 22 or decrease in ambient light. Indeed, even if operation is such that sensor 90 is OFF and sensor 92 is ON, the passage of an air bubble will first change sensor 90 to an ON condition before affecting sensor 92. Thus, for at least an instant, there will be a return to the initial ON-ON condition. In this manner, when an initially clear fluid is in the line, it can be seen that the apparatus is rendered insensitive to the opalescence of a fluid passing through the I.V. tube and to a decrease in the ambient light level.

TABLE II

| Sensor Condition: Initially Opaque Fluid | | | |
|---|---|---|---|
| | Opaque Fluid in Line | Decreased Opacity or Increase in Ambient Light | Air-in-Line |
| First Sensor (direct) | OFF | OFF | ON |
| Second Sensor (refracted) | OFF | ON | OFF |
| | | NO ALARM | ALARM |

Table II is arranged to show a situation wherein the inline fluid is initially opaque. When starting with an opaque fluid, a decrease in the opalescence or opacity of the fluid causes the second sensor, sensor 92, to turn ON before first sensor 90 because it requires less light to be activated. As also seen in Table II, an effective increase in ambient light level may also cause sensor 92 to turn ON for the same reason. As expected, when opaque fluid is in line 22, a decrease in the ambient light has no effect on sensors 90 and 92 since they are already in the OFF condition. In any of these situations, there is a safe operation and no alarm should be indicated. As the air-in-line condition is encountered, however, the sensor 90 changes to an ON condition because the air bolus or bubble allows for the passage of light on the direct optical path between emitter 30 and detector 40. As air passes sensor 92, it will remain OFF because the air will not refract the light from emitter 32 so as to be received by optical detector 42. Again, as in the situation with an initially clear fluid, air in the line causes sensor 90 to be ON and sensor 92 OFF. An alarm condition is indicated.

A comparison of Table I and Table II indicates that from either an ON-ON or an OFF-OFF condition for sensors 90 and 92, the change to an ON condition for sensor 90 and an OFF condition for sensor 92 indicates air-in-line. As will be appreciated by those skilled in the art, all other sequences of changes in the sensors can be neglected by the logic circuitry in a manner that only the air-in-line condition activates an alarm or stops operation of the infusion apparatus.

TABLE III

| Sensor Condition: Initially Opalescent or Translucent Fluid | | | |
|---|---|---|---|
| | Opalescent or Translucent Fluid in Line | | Air-in-Line |
| First Sensor (direct) | ON | OFF OFF | ON |
| | | or or | |
| Second Sensor (refracted) | ON | OFF ON | OFF |
| | NO ALARM | | ALARM |

For completeness, Table III indicates the situation in which an opalescent or translucent fluid is initially present in the fluid line 22. As seen in Table III, the relative conditions of sensors 90 and 92 may be ON-ON, OFF-OFF or OFF-ON depending upon whether the fluid is relatively clear, relatively opaque or somewhere in between. Regardless, the same logic discussed above applies here in getting sensor 90 to the ON condition and sensor 92 to the OFF condition to alarm the system.

Redundancy can be built into the system by selectively providing additional sensors arranged in a sequence to provide for the creation of signals in accordance with the logic discussed above. More specifically, in the preferred embodiment, a plurality of light emitters and their respective light detectors arranged as shown in FIGS. 8a, b, c and d comprise a series of optical sensors. Further, it can be appreciated that detectors 40, 46 and 48 are arranged to respectively receive direct light diametrically across the lumen of tube 22 from emitters 30, 36 and 38. Also, it should be appreciated that detectors 42 and 44 are positioned to receive refracted light from emitters 32 and 34 which are positioned to beam light at the periphery of the fluid flow path as fluid flows through the tube 22.

A discussion of the switching logic for light emitters 34 and 36 and their respective detectors 44 and 46 requires that, as between detectors 44 and 46, detector 44 is selected to have higher light sensitivity. Accordingly, under the same lighting conditions detector 44 will detect light at lower intensity levels than detector 46. This, of course, permits a similar insensitivity for either fluid opacity or changes in ambient light levels to the insensitivities previously discussed for sensors 90 and 92.

For the present invention, the logic circuitry always considers the ON-OFF conditions of any two adjacent detectors. With standard I.V. tubes which have relatively small inner diameters, it has been determined that air bubbles that affect only one optical sensor at a time pose negligible risk to the patient. As will be appreciated by the skilled artisan, for any given size of I.V. fluid line the spacing of the optical sensors along the fluid line 22 can be adjusted to detect larger or smaller air bubbles according to the desires of the operator.

While the particular air-in-line detector as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the apended claims.

I claim:

1. An air detector for automatically determining the presence of air in a fluid line comprising:
   means for supporting a portion of the fluid line in a position to be detected;
   a first optical sensor having a first ON-OFF means mounted on said support means and operatively associated with the supported portion of the fluid line to generate an ON signal when air or a relatively transparent fluid is in the fluid line;
   a second optical sensor having a second ON-OFF means requiring less light intensity for its ON condition than said first ON-OFF means, said second ON-OFF means mounted on said support means and operatively associated with the supported portion of the fluid line to generate an OFF signal when air or a relatively opaque fluid is in the fluid line; and
   means operatively coupled to said first and second means to alarm and indicate air in the fluid line only when simultaneously said first ON-OFF means indicates ON and said second second ON-OFF means indicates OFF.

2. An air detector as cited in claim 1 wherein said first ON-OFF means is an optical sensor comprising a light emitter and a light detector and said second ON-OFF means is an optical sensor comprising a light emitter and a light detector.

3. An air detector as cited in claim 2 wherein said light detector of said first ON-OFF means depends on direct light from said emitter of said first ON-OFF means for its ON condition, and said light detector of said second ON-OFF means depends on refracted light from said emitter of said second ON-OFF means for its ON condition.

4. An air detector as cited in claim 1 further comprising:
   a third optical sensor having a third ON-OFF means mounted on said support means adjacent said second ON-OFF means and axially opposite said first ON-OFF means and operatively associated with the supported portion of the fluid line to generate an OFF signal when air or a relatively opaque fluid is in the fluid line;
   a fourth optical sensor having a fourth ON-OFF means requiring more light intensity for its ON condition than said third ON-OFF means, said fourth ON-OFF means mounted on said support means adjacent said third ON-OFF means and axially opposite said second ON-OFF means and operatively associated with the supported portion of the fluid line to generate an ON signal when air or a relatively clear fluid is in the fluid line; and
   means operatively coupled to said third and fourth ON-OFF means to alarm and indicate air in the fluid line only when simultaneously said third means indicates OFF and said fourth means indicates ON.

5. An air detector as cited in claim 4 wherein said first ON-OFF means is an optical sensor comprising a light emitter and a light detector, said second ON-OFF means is an optical sensor comprising a light emitter and a light detector, said third ON-OFF means is an optical sensor comprising a light emitter and a light detector, and said fourth ON-OFF is an optical sensor comprising a light emitter and a light detector.

6. An air detector as cited in claim 5 wherein said detectors of said first and said fourth ON-OFF means depend on direct light from said emitters of said first and said fourth ON-OFF means for the ON condition, and said detectors of said second and said third ON-OFF means depend on refracted light from said emitters of said second and said third ON-OFF means for the ON condition.

7. An air detector for automatically determining the presence of air in a fluid line comprising:
   means for supporting a portion of the fluid line in a position to be detected;
   a first optical sensor having a first ON-OFF means mounted on said support means and operatively associated with the fluid line for producing an ON signal when air or a relatively transparent fluid is in the fluid line;
   a second optical sensor having a second ON-OFF means requiring less light intensity for its ON condition than said first ON-OFF means, said second ON-OFF means mounted on said support means and operatively associated with the fluid line downstream from said first means, for producing an OFF signal when air or a relatively opaque fluid is in the fluid line;
   a third optical sensor having a third ON-OFF means requiring more light intensity for its ON condition than said second ON-OFF means, said third ON-OFF means mounted on said support means and operatively associated with the fluid line, downstream from said second means, for producing an ON signal when air or a relatively transparent fluid is in the fluid line; and
   means operatively coupled to said first, second and third ON-OFF means to alarm only whenever said second means indicates OFF simultaneously when either said first or said third means indicates ON.

8. An air detector as cited in claim 7 wherein said first ON-OFF means and said third ON-OFF means depend on direct light for the ON condition and said second ON-OFF means depends on refracted light for the ON condition.

9. An air detector for automatically determining the presence of air in a fluid line comprising:
   means for supporting a portion of the fluid line in a position to be detected;
   a first ON-OFF optical sensor operatively associated with the fluid line for producing ON signals in accordance with the reception of light directed diametrically through the portion of the fluid line mounted on said support means;
   a second ON-OFF optical sensor operatively associated with the fluid line and having a relatively lower light intensity threshold for changing between the ON and OFF conditions than said first ON-OFF means for producing ON signals in accordance with the reception of light refracted by fluid in the fluid line; and
   means operatively coupled to said first and said second optical sensors to provide an alarm signal only when simultaneously said first means produces an ON signal and said second means produces an OFF signal.

10. An air detector as cited in claim 9 wherein said means for producing an alarm signal is a microprocessor.

* * * * *